United States Patent [19]

Dahod et al.

[11] Patent Number: 4,668,628
[45] Date of Patent: May 26, 1987

[54] RESOLUTION OF RACEMIC MIXTURES OF ALIPHATIC ACID ESTERS

[75] Inventors: Samun K. Dahod, Yorktown Heights, N.Y.; Patricia Siuta-Mangano, Ramsey, N.J.

[73] Assignee: Stauffer Chemical Company, Westport, Conn.

[21] Appl. No.: 718,600

[22] Filed: Apr. 1, 1985

[51] Int. Cl.$^4$ .......................... C12P 7/52; C07P 41/00
[52] U.S. Cl. ................................. 435/135; 435/136; 435/141; 435/280
[58] Field of Search ............... 435/135, 136, 141, 280

[56] References Cited

FOREIGN PATENT DOCUMENTS 0094295 6/1982 Japan .................................. 435/280

OTHER PUBLICATIONS

Iriuchijima et al., *Agri. Biol. Chem.*, 45(6), 1389-1392 (1981).
Marsheck et al., *Biochimica et Biophsica Acta*, 316 (1973), 363-365.
Oritani et al., *Agr. Biol. Chem.*, 38(10), 1965-1971, 1974.
McGahren et al., *J. Org. Chem.*, vol. 42, No. 9, 1977, 1659-1660.
Mori et al., *Tetrahedron*, 36, pp. 91-96, (1980).
Kawai et al., *Tetrahedron Letters*, 22, No. 27, pp. 2527-2530, (1981).
Iriuchijima et al., *Agric. Biol. Chem., 46(5), 1153-1157, (1982)*.
Iriuchijima et al., *Agric. Biol. Chem.*, 46(6), 1593-1597, (1982).
Gaffield et al., *Tetrahedron*, 27, pp. 915-934 (1971).
Cambou et al., *Biotech. and Bioeng.*, vol. XXVI, pp. 1449-1454 (1984).
Lavayre et al., *Biotech. and Bioeng., vol. XXIV, pp. 2175-2187 (1982)*.
Cambou et al., *Applied Biochem. & Biotech.*, vol. 9, (1984) pp. 255-260.
Brockerhoff, Abstract vol. 72 (1970), 18681u.
Savary, Abstract vol. 76 (1972), 11500h.

*Primary Examiner*—Christine M. Nucker
*Attorney, Agent, or Firm*—Paul J. Juettner

[57] ABSTRACT

Racemic mixtures of partially water-soluble esters defined by the formula

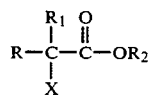

wherein
R and $R_1$ represent hydrogen and $C_1$-$C_4$ alkyl;
$R_2$ represents $C_1$-$C_4$ alkyl and
X represents halogen, aliphatic or aromatic groups and substituted derivatives thereof wherein R, $R_1$ and X are different can be resolved by reducing the water solubility of a racemic mixture of said esters by means other than changing the chemical composition of the ester, contacting the racemic mixture of esters of reduced water solubility with a lipase enzyme from *Candida cylindracea* capable of stereospecifically resolving the racemic mixture of hydrolysis and stereospecifically resolving the racemic mixture.

21 Claims, No Drawings

4,668,628

RESOLUTION OF RACEMIC MIXTURES OF ALIPHATIC ACID ESTERS

FIELD OF THE INVENTION

The present invention relates to a process for resolving racemic mixtures of water soluble chiral esters.

BACKGROUND OF THE INVENTION

Certain herbicides such as napropamide, chemical name 2-(alpha-naphthoxy)-N-N-diethylpropionamide, are active only in the dextro (+) isomeric form. (Synthesis and Herbicidal Activity of N,N-Diethyl-2-(1-naphthyloxy)propionamide & Its Optical Isomers—Agricultural & Food Chemistry, Vol. 23, 5 (September-/October 1975) pp 1008–1010). The herbicide is presently prepared in a racemic mixture which results in lost raw material and lost manufacturing time as the levo (−) isomeric form is inert. While it is economically desirable to produce only the dextro isomer form, the prior art lacks a method for economically preparing the desired isomer.

It is known that the dextro isomer can be prepared from L-methyl-2-chloropropionate. This isomer is not presently available at a price which can be economically utilized in the process of preparing napropamide.

Various enzymes have shown stereospecificity in resolving specific substrates by hydrolysis, e.g., chymotrypsin, for resolving D,L-phenylalanine esters.

Lipase enzyme is known to hydrolyze fats into fatty acids and glycerol. No stereospecificity is involved.

By private communication it is known that the octyl ester of 2-chloropropionic acid can be resolved by lipase from *Candida cylindracea* (Lipase-catalyzed Production of Optically Active Acids Via Asymmetric Hydrolysis of Esters: Effect of the Alcohol Moiety—Bernard Cambou and Alexander M. Klibanov). The communication confirmed our earlier work that methyl 2-chloropropionate could not be stereospecifically hydrolyzed using lipase enzyme. The theory of successful operation given in the communication is that the octyl ester is insoluble in water whereas the methyl ester is soluble in water.

A recent publication shows the stereospecific resolution of methyl 2-(p-chlorophenoxy)propionate with lipase from *Candida cylindracea*. Comparison of Different Strategies for the Lipase Catalyzed Preparative Resolution of Racemic Acids and Alcohols: Asymmetric Hydrolysis, Esterification and Transesterification. Cambou, B. & Klibanov, A. M. Biotechnology and Bioengineering, Vol. XXVI, pp. 1449–1454 (1984). Methyl 2-(p-chlorophenoxy)propionate is not partially water soluble as defined herein. The article does not show any problems in stereospecific resolution by hydrolysis.

THE INVENTION

It has now been found that water-soluble chiral esters can be resolved by a process comprising partially insolubilizing the water-soluble chiral ester and hydrolyzing the partially water insolubilized chiral ester with a lipase enzyme. The insolubilization can be by the use of an organic solvent for the ester which solvent is insoluble in water, by the use of salts and buffers or any other means of insolubilizing the chiral ester relative to the aqueous component during the enzymatic hydrolysis. Insolubilization can also be affected or improved by temperature manipulation.

Various other features including preferred lipase sources, reaction conditions and substrates will be discussed in the text which follows.

DETAILED DESCRIPTION OF THE INVENTION

The water soluble chiral ester substrates which can be resolved in accordance with the invention can be represented by the formula $$R-\underset{\underset{X}{|}}{\overset{\overset{R_1}{|}}{C}}-\overset{\overset{O}{\|}}{C}-OR_2 \qquad I$$

wherein

R and $R_1$ can be hydrogen and $C_1$–$C_4$
$R_2$ ca be $C_1$–$C_4$ alkyl; and
X can be halogen (fluorine, chlorine, bromine or iodine), aliphatic or aromatic groups and substituted derivatives thereof wherein R, $R_1$, and X are different. Preferably, R and $R_2$ are independently $C_1$–$C_2$ and more preferably $C_1$. $R_1$ is preferably hydrogen, X is preferably halogen and more preferably halogen of chlorine or bromine. The brominated compound is less soluble than the chlorinated compound.

While compounds such as methyl 2-(p-chlorophenoxy)propionate are sufficiently insoluble in water to allow resolution by enzymatic hydrolysis, other substituted compounds such as methyl 2-(p-hydroxyphenoxy)propionate and methyl 2-(p-hydroxyphenyl)propionate are sufficiently water soluble as defined herein to cause difficulties in stereospecific resolution by hydrolysis. The invention is directed to processes for resolving these compounds without chemically changing the substrate compound.

By aliphatic or aromatic groups and substitute derivatives thereof, it is intended to mean only compounds of formula I having those groups which are partially soluble in water as defined herein. These groups can include phenyl, hydroxyphenyl, phenoxy, hydrophenoxy, methyl, ethyl, chloromethyl, hydroxyethyl and the like, provided that the compounds containing these groups are at least partially water soluble.

Illustrative of the chiral compounds which can be resolved are:
methyl-2-chloropropionate
methyl-2-bromopropionate
ethyl-2-chloropropionate
ethyl-2-bromopropionate
propyl-2-chloropropionate
butyl-2-chlorobutylate
methyl-2-phenoxypropionate The brominated compound is less soluble than the chlorinated compound.

The esters are at least partially soluble in water. By "partially soluble" is meant that the ester must be soluble to more than 25 millimolar in water at 25° C. The esters must be capable of being made substantially water insoluble without changing the chemical composition of the esters. The esters must be soluble in an organic phase which is insoluble in water or capable of being insolublized, i.e., soluble in water to less than 25 millimolar, in water by salts or any other procedure used to accomplish that end. The ester must be hydrolyzable by the lipase enzyme to form the corresponding free acid. The invention will be discussed in connection with the preferred compounds, the 2-halopropionates.

The lipase for use in resolving the chiral esters of the invention is obtained from the yeast *Candida cylindracea*. This enzyme has been found to produce the highest yield of resolved isomers in the process of the invention and is considered the most desirable for a commercial process.

More effective stereospecific hydrolysis requires that the soluble ester be substantially insolubilized, i.e., the substrate is soluble in water to less than 25 millimolar. Any method for insolubilizing the ester without changing its chemical composition can be used. An organic water-insoluble solvent for the ester can be used to dissolve the ester. The solvent solution is then admixed with an aqueous solution of the enzyme. Preferably, the mixture is agitated sufficiently to finely disperse one phase in the other.

The substantially water immiscible inert organic solent material is a solvent for the racemate. By "immiscible" it is intended to mean that the organic solvent is miscible in the water up to no more than 5 percent and preferably no more than 2 percent under the conditions of reaction. The organic material can be any water immiscible or partially miscible organic solvent which is non-reactive with the chiral ester substrate or the lipase enzyme and which has substantially no adverse effect on the enzyme. The organic solvents can be illustrated by perchloroethylene, carbon tetrachloride, toluene, hexane (either normal or cyclo-), trichloroethylene, 1,2-dichloroethane, fluorochloroethanes, and the like, with perchloroethylene and carbon tetrachloride being preferred. Solvents such as trichloroethylene and 1,2-dichloroethane are less preferred with the preferred lipase from *Candida cylindracea* as they appear to slow the rate of hydrolysis. The solvent to water volume ratio can range from about 10:1 to about 1:10 with a ratio of from about 3:1 to about 1:5 being preferred. The chiral ester substrate content of the organic solvent can range from about 2.5 percent to about 70 percent, with from about 10 percent to about 60 percent on a weight per volume basis being preferred.

The racemic esters can also be temporarily insolubilized in aqueous solution by means of a quantity of salt sufficient to reduce the solubility of the substrate in the water to less than 25 millimolar. Representative examples of effective salts include the halides, carbonates, bicarbonates, phosphates, sulfates, nitrates and mixtures thereof of alkali metal and alkaline earth metals. The salt must be at least partially water soluble. Suitable salts are illustrated by sodium chloride, potassium chloride, sodium bicarbonate, sodium sulfate and the like.

Since the pH of the medium becomes more acidic as the hydrolysis proceeds due to the formation of the D-acid, it is desirable to maintain the pH throughout the term of the hydrolysis substantially within a range conducive to enzyme hydrolysis, i.e., about pH 4–8. While direct addition of a neutralizing agent, e.g. sodium hydroxide, can be used, it is less preferred as the addition can create localized points of elevated pH where hydrolysis is not stereospecific. Yields of resolved product are reduced. The hydrolysis reaction medium is preferably buffered to maintain pH control. Buffers which can be used include phosphates, carbonates, bicarbonates, borates and organic buffers such as tris(hydroxymethyl)aminomethane. In the most preferred form of the invention the insolubilizing salt can also act as the buffer.

A preferred material accomplishing these two ends is sodium or potassium bicarbonate, as well as calcium carbonate. The most preferred is the bicarbonate.

Lipase enzyme is normally used in combination with small quantities of buffer and sodium chloride insufficient in quantity to decrease solubility of the ester, i.e., from about 50 to about 200 millimolar sodium chloride. The salt used in insolubilizing the water soluble ester and/or buffering can be used in an amount ranging from about 5 percent to about 40 weight percent based on the weight of the water.

The lipase can be added in a pure or crude form. The lipase can also be immobilized using well known techniques. Immobilized enzyme can be used to economically provide a higher level of enzyme per substrate amount since the enzyme can be isolated at the conclusion of the reaction and recycled for further use.

The temperature maintained within the hydrolysis media is favorable for the hydrolysis reaction with the enzyme being used. In connection with the lipase enzyme from *Candida cylindracea*, the temperature of reaction can range from about 0° C. to about 40° C. The use of lower temperatures (from 2°–8° C.) are preferred as they contribute to maintaining the substrate insoluble even though the lower temperatures are less conducive to maximum enzyme reactivity. Variations in the parameters for effectively using the enzyme can be easily determined by a skilled artisan.

The lipase can be used in an amount sufficient to provide an enzyme activity ranging from about 1 to about 50 International Units/milligram of the substrate ester. The definition of a unit is that quantity of enzyme which can release 1 microequivalent of fatty acid from a triglyceride in 1 minute at pH 7.7 and 37° C.

The hydrolysis reaction can be conducted for a period of time ranging from about 1 to about 120 and preferably from about 8 to about 60 hours. Extensive hydrolysis may be detrimental to resolution as resolved acid may be racemized in the aqueous medium. The activity of the enzyme can be gradually affected by the product alcohol or the solvent.

The methods of insolubilization can be used separately or in combination. The salt or solvent can be used singly but are desirably used together. Thus, a solvent such as carbon tetrachloride can be used with an insolubilizing agent and/or buffer such as sodium bicarbonate. Because of the dual insolubilization effect, the solvent can be used in lower amounts.

The hydrolysis process is conducted under sufficient agitation to maintain the reactants sufficiently in contact such that the reaction can occur. While the degree of agitation is not critical, agitation is preferably strong enough to form finely dispersed droplets of one phase in the other. Agitation formed by pumping fractions in and out of the reactor is acceptable. The hydrolysis proceeds more effectively in an agitated state since the use of a buffer salt like sodium bicarbonate may collect on the bottom of the reactor due to its limited solubility. For these reasons, a batch procedure is preferred.

The resolved product, the D-isomer acid, is water soluble and collects in an aqueous phase. The organic phase is enriched with the L-isomer ester. The D-isomer acid can be recovered from the aqueous phase by any known technique including solvent extraction.

The L-isomer ester is a known compound which can be used as an intermediate in the preparation of known compounds. For instance, D-isomer of the herbicide napropamide can be prepared by condensing L-methyl 2-chloropropionate with alpha naphthol followed by reaction with diethyl amine.

The D-isomer acids can be utilized to prepare D-2-phenoxypropionic acid herbicide as described in British Pat. No. 1,114,040. If the L-ester is the desired product, the D-isomer acid can be reesterified and racemized to start a new reaction batch. If the D-acid is the desired product, the L-ester could be racemized for further resolution.

The invention is illustrated in the following Examples:

EXAMPLE 1

21.5 grams of D,L-methyl-2-chloropropionate was added to 90 milliliters of 0.2 molar potassium phosphate buffer solution at pH 7.0 saturated with sodium chloride. The stirred emulsion was supplemented by a lipase from yeast *Candida cylindracea* (total activity=736 International Units, total protein=67 milligrams, lipase:substrate (wt:wt)=1:321). The pH was maintained at pH 7.0 with the addition of 5N sodium hydroxide through a pH control system.

After 42 hours and a consumption of 21 milliliters of 5N sodium hydroxide, the reaction was stopped. Unreacted L-methyl-2-chloropropionate was separated by centrifugation and monitored for optical purity and yield of the reaction. The optical rotation on this sample was $-19.492°$ indicating that the product was 84 percent of the L-isomer ester and 16 percent of the D-isomer of methyl-2-chloropropionate. (The alpha D rotation for a standard at 25° C. is $-26.8°$, density=1.075 g/ml.) The yield of the reaction was 40 percent.

EXAMPLE 2

10.75 grams (88 millimoles) D,L-methyl-2-chloropropionate was dissolved in 40 milliliters of carbon tetrachloride. The organic phase was dispersed in 50 milliliters of water containing 4.43 grams of sodium bicarbonate and 20 milligrams of *Candida cylindracea* yeast lipase (total activity=220 International Units, lipase:substrate (wt:wt)=1:538). The mixture was stirred vigorously at 4° C. for 18 hours.

The carbon tetrachloride phase was separated and monitored for optical purity of unhydrolyzed methyl-2-chloropropionate and the yield of the reaction. The optical rotatory power revealed that the methyl-2-chloropropionate was 92 percent of the L-isomer and 8 percent of the D-isomer. (Alpha D rotation at 25° C. is $-25.58°$ compared to a standard of $-30.45°$ in carbon tetrachloride.) The yield of enzymatic conversion was determined by reacting an aliquot of the carbon tetrachloride layer with carboxyl esterase, a nonspecific esterase. A yield of 35 percent was obtained (50 percent is theoretical).

EXAMPLE 3

29.94 grams of D,L-methyl-2-bromopropionate, 60 milliliters of water, 8.25 grams sodium bicarbonate, and 80 milligrams of yeast lipase enzyme from *Candida cylindracea* (total activity=878 International Units, lipase:substrate ratio (wt:wt)=1:374) were incubated with vigorous agitation at 4° C. for 48 hours.

The organic and aqueous phases were separated and unreacted methyl-2-bromopropionate was recovered as the organic phase. The optical rotation of this organic phase was $-63.95°$. (Alpha D rotation for a standard at 25° C. is $-55.5°$, density=1.49 g/ml.) This indicated 89 percent of the L-isomer and 11 percent of the D-isomer.

The aqueous phase was evaporated after adjusting the pH down to 2.0. The viscous liquid obtained this way had an Alpha D rotation at 25° C. of $+15.0$ (methanol, C=10.7) indicating an excess of D-2-bromopropionic acid over L-2-bromopropionic acid.

EXAMPLE 4

A. 6.13 grams (50 millimoles) of D,L-methyl-2-chloropropionate was dissolved in 44.3 milliliters of carbon tetrachloride in a 150 milliliter stoppered Erlenmeyer flask. The organic phase was dispersed in 49.2 milliliters of a 0.75 molar sodium phosphate buffer solution at pH 8.2 at 4° C.

The stirred emulsion was supplemented by a solution of lipase from yeast *Candida cylindracea* (total activity=168 International Units, total protein=15.3 milligrms, lipase:substrate (wt:wt)=1:400).

After a 44 hour reaction, the organic phase was monitored for optical purity of unhydrolyzed methyl-2-chloropropionate and the yield of the reaction. The optical rotatory power revealed that the methyl-2-chloropropionate was 96 percent of the L-isomer. (Alpha D rotation at 25° C. is $-28.01°$ compared to a standard of $-30.45°$ in carbon tetrachloride.) The yield of the enzymatic conversion was 27 percent.

B. This example, repeated using 48.3 milliliters of a 0.6 molar sodium phosphate buffer, twice the lipase (336 International Units) at room temperature for 16 hours, gave 41 percent yield and 88 percent L-isomer.

EXAMPLE 5

A reactor, equipped with a thermostatic jacket having an inlet for an electrode for pH readings, a thermometer, and an inlet for the addition of 5N NaOH was charged with 28.5 milliliters carbon tetrachloride, 23.1 grams D,L-methyl-2-chloropropionate (190 millimoles) and 50 milliliters composed of 5 millimolar sodium phosphate buffer solution at pH 7.0 (4° C.) and *Candida cylindracea* yeast lipase (total activity=411 International Units, total protein=38.5 milligrams, lipase:substrate (wt:wt)=1:600). The pH was monitored at pH 7.0 by the automatic instrumental addition of sodium hydroxide.

After 4 days and a consumption of 22.24 milliliters of 5N sodium hydroxide, the reaction was discontinued. The yield and optical purity, determined as in Example 2 was 40 percent and 92 percent (Alpha D rotation at 25° C.=$-25.6°$), respectively.

EXAMPLE 6

A. 11.4 grams (95 millimoles) of D,L-methyl-2-chloropropionate were dissolved in 14.4 milliliters of perchloroethylene. The organic phase was dispersed in 46.3 milliliters of 50 millimolar sodium chloride containing 2.61 grams of calcium carbonate at 4° C.

The stirred emulsion was supplemented from *Candida cylindracea* lipase (304 International Units, 28.5 milligrams, lipase:substrate (wt:wt)=1:400).

After 17 hours, the solvent phase was monitored for optical purity of unhydrolyzed methyl-2-chloropropionate and the yield of the reaction. The optical rotation revealed that the product was 75 percent L-isomer (Alpha D rotation at 25° C.=$-17.0°$, compared to standard=$-34.0°$ in percloro-ethylene). The yield of the reaction was 49 percent.

B. This example was repeated at room temperature. The yield was 44 percent and the optical rotation revealed the product was 76 percent L-isomer.

EXAMPLE 7

The procedure of Example 4 was repeated using various molarities of methyl-2-chloropropionate, buffers and ratios of enzyme to substrate (E:S) at various temperatures. 50 milliliters of buffer was used in each case except Sample K where 40.7 milliliters was used. The following results were obtained:

TABLE I

| Sample | MCP Molarity* | Buffer | Time (Hours) | E:S | % Yield | % L-MCP |
|---|---|---|---|---|---|---|
| 0° C. | | | | | | |
| A | 3.8 M | CaCO₃ | 24 | 1:400 | 42 | 88 |
| 4° C. | | | | | | |
| B | 1.0 M | NaPi** (600 mM, pH 8.2) | 16 | 1:200 | 38 | 94 |
| C | | NaPi** (600 mM, pH 8.2) | 16.5 | 1:300 | 45 | 85 |
| D | | (750 mM, pH 8.2) | 113 | 1:400 | 29 | 100 |
| E | | NaPi** (600 mM, pH 8.2) | 44 | 1:800 | 49 | 80 |
| F | | CaCO₃ | 17 | 1:400 | 53 | 82 |
| G | 2.0 M | NaPi (1.2 M, pH 8.4) | 41.75 | 1:200 | 42 | 83 |
| H | | NaPi** (1.2 M, pH 8.4) | 41.75 | 1:400 | 45 | 85 |
| I | | CaCO₃ | 17 | 1:400 | 44 | 85 |
| J | 3.8 M | CaCO₃ | 17 | 1:400 | 46 | 85 |
| K | 5.0 M | pH Stat*** | 29 | 1:200 | 38 | 94 |
| 25° C. | | | | | | |
| L | 1.0 M | Napi (600 mM, pH 8.2) | 16 | 1:200 | 41 | 88 |
| M | | (1.25 M, pH 8.1) | 23 | 1:400 | 54 | 78 |
| N | 3.8 M | CaCO₃ | 17 | 1:400 | 41 | 81 |

*To avoid repetition of conditions, conditions only listed where a change occurs. All empty spaces beneath a condition are considered to be the same as the last preceding number in the columns.
**NaPi is intended to mean a sodium phosphate buffer (mono and di basic) orthophosphate of equal molarities.
***pH Stat is intended to mean continuous potentiometric titration to a consistent pH level.

EXAMPLE 8

The procedure of Example 4B. was repeated using a 1.0 molar solution of various D,L-propionate esters at 25° C. in a carbon tetrachloride/aqueous system with an enzyme to substrate ratio of 1:100.

The following results were obtained:

TABLE II

| Ester | % Yield | % L-ester |
|---|---|---|
| Methyl | 48 | 81 |
| Ethyl | 47 | 66 |
| Propyl | 54 | 77 |
| Butyl | 52 | 72 |

EXAMPLE 9

Example 4B. was repeated using various solvents, 1.0 molar solution of D,L-methyl-2-chloropropionate, NaPi buffer at an aqueous to organic solvent ratio of 1:1 and 27 hours at 25° C. with the following results:

TABLE III

| Ex. No. | Solvent | Degree of Rxn. % | Yield % | % L MCP | % D MCP |
|---|---|---|---|---|---|
| A | Carbon tetrachloride | 63 | 37 | 92 | 8 |
| B | Perchloroethylene | 73 | 27 | 93 | 7 |
| C | Toluene | 64 | 36 | 64 | 36 |
| D | Methylene Chloride | 29 | 71 | 51 | 49 |
| E | Trichloroethylene | 14 | 86 | 55 | 45 |
| F | 1,2-dichloroethane | 5 | 95 | 52 | 48 |

From this data the solvents in A, B and C were operative. The solvent in D did not appear to be operative under the conditions of reaction. The solvents of E and F were marginal as the hydrolysis rates were low.

EXAMPLE 10

The process of Example 1 was repeated using 50 millimolar D,L-methyl-2-chloropropionate, 120 millimolar sodium phosphate buffer pH 7.2 and no organic solvent. The buffer was not used in an amount sufficient to salt out the racemate. The hydrolysis was conducted at 25° C. for 10 minutes using an enzyme (*Candida cylindracea*) to substrate ratio of 1:10. The reaction hydrolysis was 36 percent with no stereospecificity.

What is claimed is:

1. A process for enzymatically resolving racemic mixtures of partially water-soluble esters which are soluble to more than 25 millimolar in water at 25° C. comprising reducing the water solubility of a racemic mixture of said esters to less than 25 millimolar by means other than changing the chemical composition of the ester, contacting the racemic mixture of esters of reduced water solubility with a lipase enzyme from *Candida cylindracea* capable of stereospecifically resolving the racemic mixture by hydrolysis and stereospecifically resolving the racemic mixture.

2. A process for enzymatically resolving racemic mixtures of partially water-soluble esters which are soluble in water to more than 25 millimolar at 25° C. defined by the formula $$R - \underset{\underset{X}{|}}{\overset{\overset{R_1}{|}}{C}} - \overset{O}{\overset{\|}{C}} - OR_2$$

wherein

R and $R_1$ represent hydrogen and $C_1$-$C_4$ alkyl;

$R_2$ represents $C_1$-$C_4$ alkyl and

X represents halogen, aliphatic or aromatic groups and substituted derivatives thereof with the proviso that the compounds are at least partially water soluble wherein R, $R_1$ and X are different comprising reducing the water solubility of a racemic mixture of said esters to below about 25 millimolar by means other than changing the chemical composition of the ester selected from the group consisting of (a) adding a salt to an aqueous solution of the lipase enzyme in which at least some of the ester is in solution in an amount sufficient to lower the solubility of the ester in the aqueous solution; and (b) a combination of (a) with a water immiscible organic solvent, contacting the racemic mixture of esters of reduced water solubility with a lipase enzyme from *Candida cylindracea* capable of stereospecifically resolving the racemic mixture by hydrolysis and stereospecifically resolving the racemic mixture.

3. The process as recited in claim 2 wherein R is $C_1$–$C_4$ alkyl, $R_1$ is hydrogen, $R_2$ is $C_1$–$C_4$ alkyl and X is halogen.

4. The process as recited in claim 2 wherein R is $C_1$–$C_2$ alkyl and $R_2$ is $C_1$–$C_2$ alkyl.

5. The process as recited in claim 2 wherein R is hydrogen, $R_1$ is methyl, and X is p-hydroxyphenyl.

6. The process as recited in claim 5 wherein $R_2$ is methyl.

7. The process as recited in claim 2 wherein R is hydrogen, $R_1$ is methyl and X is p-hydroxyphenoxy.

8. The process as recited in claim 7 wherein $R_2$ is methyl.

9. The process as recited in claim 3 wherein R and $R_2$ are each methyl.

10. The process as recited in claim 9 wherein X is chlorine.

11. The process as recited in claim 2 wherein X is a halogen of chlorine or bromine.

12. The process as recited in claim 2 wherein said solvent is selected from the group consisting of carbon tetrachloride, perchloroethylene and mixtures thereof.

13. The process as recited in claim 8 wherein said solvent is carbon tetrachloride.

14. The process as recited in in claim 2 wherein said salt is an at least partially water-soluble salt selected from the group consisting of alkali metal and alkaline earth metal halides, carbonates, bicarbonates, phosphates, sulfates, nitrates and mixtures thereof.

15. The process as recited in claim 14 wherein said salt is sodium chloride, sodium bicarbonate or mixtures thereof.

16. The process as recited in claim 2 wherein said esters are 2-chloropropionic acid esters.

17. The process as recited in claim 16 wherein said solvent is selected from the group consisting of carbon tetrachloride perchloroethylene and mixtures thereof.

18. The process as recited in claim 16 wherein said salt is sodium chloride, sodium bicarbonate or mixtures thereof.

19. The process as recited in claim 16 wherein the ester is methyl.

20. The process as recited in claim 16 wherein said racemate is resolved using said water insoluble solvent in combination with said insolubilizing salt.

21. The process as recited in claim 20 wherein the temperature of hydrolysis ranges from about 2° C. to about 8° C.

* * * * *

UNITED STATES PATENT AND TRADEMARK OFFICE
CERTIFICATE OF CORRECTION

PATENT NO. : 4,668,628

DATED : May 26, 1987

INVENTOR(S) : Samun K. Dahod et al.

It is certified that error appears in the above-identified patent and that said Letters Patent are hereby corrected as shown below:

Abstract, last line from bottom, "of" should be --by--;

Col. 2, line 21, "ca" should be --can--;

Col. 6, line 17, "milligrms" should be --milligrams--;

Col. 6, line 25, "27%" should be --37%--;

Col. 6, line 41, "monitored" should be --maintained--;

Col. 7, Table I, delete what is shown for Samples D, E, G, L, and M under the heading "Buffer" and substitute:

| --Sample | Buffer |
|---|---|
| D | NaPi** (750 mM, pH 8.2) |
| E | NaPi** (750 mM, pH 8.2) |
| G | NaPi** (1.2 M, pH 8.4) |
| L | NaPi** (600 mM, pH 8.2) |
| M | NaPi** (1.25 M, pH 8.1)--; |

UNITED STATES PATENT AND TRADEMARK OFFICE
CERTIFICATE OF CORRECTION

PATENT NO. : 4,668,628
DATED : May 26, 1987
INVENTOR(S) : Samun K. Dahod et al.

It is certified that error appears in the above-identified patent and that said Letters Patent are hereby corrected as shown below:

Col. 10, line 3, delete the second instance of "in"--;
Col. 10, line 15, insert a comma (,) after "tetrachloride";
Col. 6, line 51, delete "95" and insert --93--.

Signed and Sealed this

Thirteenth Day of October, 1987

Attest:

DONALD J. QUIGG

Attesting Officer

Commissioner of Patents and Trademarks